United States Patent
Connors

(10) Patent No.: US 7,887,703 B2
(45) Date of Patent: Feb. 15, 2011

(54) DIALYSIS APPARATUS AND A METHOD FOR ASSEMBLING A DIALYSIS APPARATUS

(75) Inventor: John F. Connors, Shrewsbury, MA (US)

(73) Assignee: Tangenx Technology Corporation, Shrewsbury, MA (US)

( * ) Notice: Subject to any disclaimer, the term of this patent is extended or adjusted under 35 U.S.C. 154(b) by 924 days.

(21) Appl. No.: 11/676,077

(22) Filed: Feb. 16, 2007

(65) Prior Publication Data
US 2008/0197066 A1    Aug. 21, 2008

(51) Int. Cl.
*B01D 63/00* (2006.01)
(52) U.S. Cl. ............... 210/321.75; 29/428; 210/321.6; 210/321.72; 422/101; 422/102; 422/104
(58) Field of Classification Search ............ 210/321.6, 210/321.72, 321.75, 321.84; 422/99, 101, 422/102, 104; 29/428
See application file for complete search history.

(56) References Cited

U.S. PATENT DOCUMENTS

| 6,776,908 | B1 | 8/2004 | Banker et al. | |
|---|---|---|---|---|
| 2005/0112033 | A1* | 5/2005 | Zhang et al. | 422/102 |
| 2007/0215538 | A1* | 9/2007 | Periana et al. | 210/321.6 |

* cited by examiner

*Primary Examiner*—John Kim
(74) *Attorney, Agent, or Firm*—Marsh Fischmann & Breyfogle LLP

(57) ABSTRACT

The invention relates to a dialysis apparatus, comprising:
  a body with two planar sides,
  wells contained in the body, the wells being accessible from one planar side,
  a plurality of membranes for separating the wells into compartments, wherein each of said membranes is isolated one from another.

16 Claims, 2 Drawing Sheets

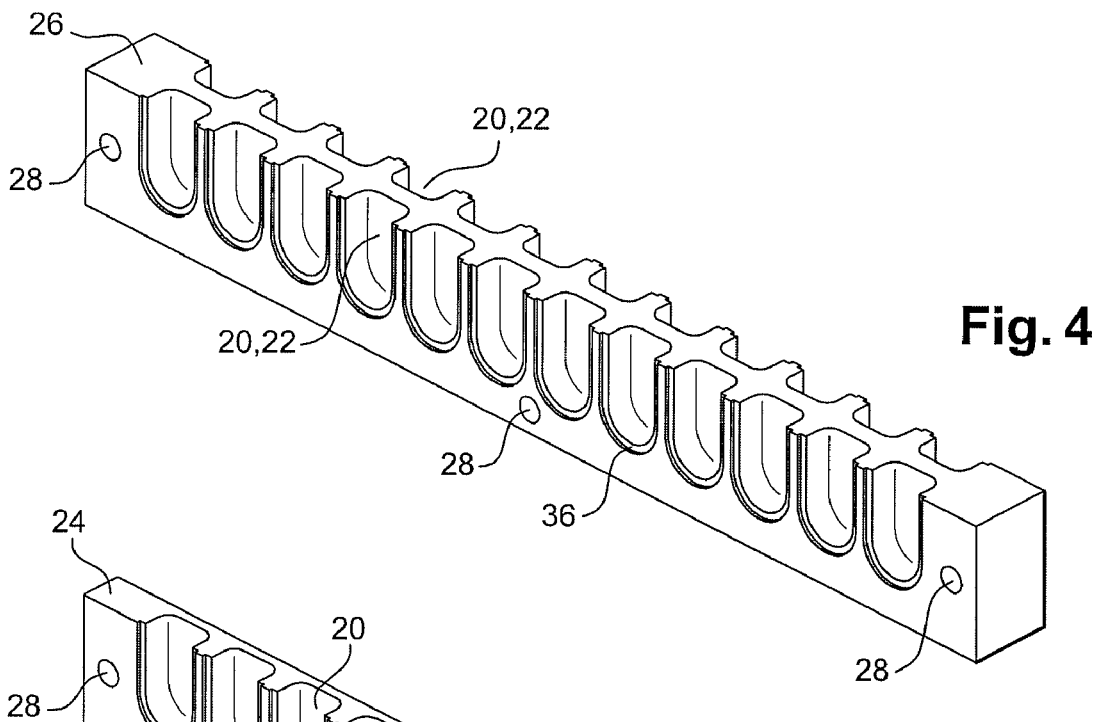
Fig. 4
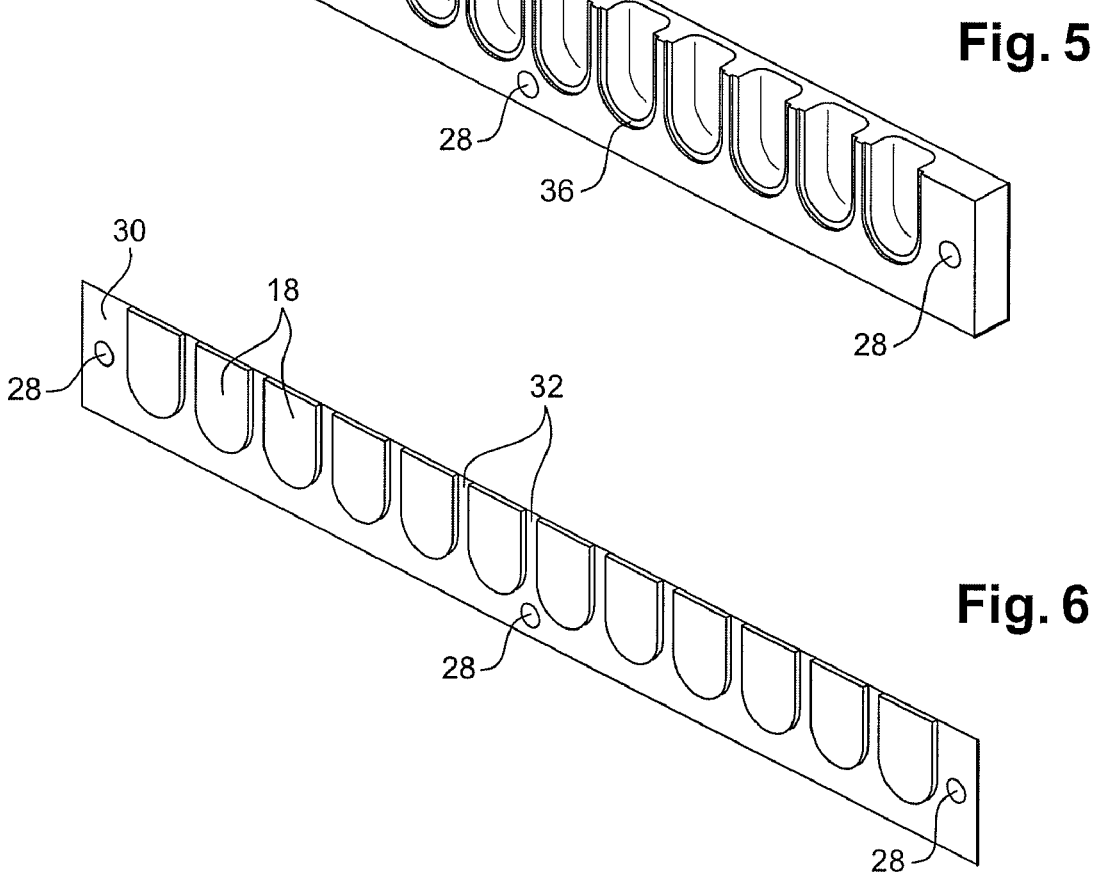
Fig. 5
Fig. 6

DIALYSIS APPARATUS AND A METHOD FOR ASSEMBLING A DIALYSIS APPARATUS

FIELD OF THE INVENTION

The present invention relates to the field of dialysis apparatuses. More particularly, the present invention relates to dialysis apparatus having a body with any number of sample wells divided into compartments by membranes. The present invention also relates to a method for assembling a dialysis apparatus.

BACKGROUND OF THE INVENTION

Equilibrium dialysis is a procedure for measuring the concentration of free, relatively small molecules in a sample. Dialysis is a separation process for substances in solution driven by a concentration gradient and utilizing their varying diffusion rates through a semi-permeable membrane. Dialysis is employed to retain large molecule while allowing the passage of small ones.

U.S. Pat. No. 6,776,908 discloses a micro-equilibrium dialysis vertically-loaded apparatus. This document states that historically, equilibrium dialysis applications, such as binding and affinity studies, have been slow, difficult and costly to perform. One of the best currently available devices for equilibrium dialysis, for example, only allows for a maximum of twenty samples to be tested simultaneously per device and requires expensive equipment which is often difficult to use and timely to assemble. The device also is not adaptable to standard 96-well pipetting equipment nor does it easily lend itself to automation through the use of robotic systems. Further, this document discloses that this currently available device utilizes oval or circular dialysis membranes which are placed on top of a hemi-spherical or cylindrical lower half of the testing cell and over which is joined the corresponding top half of the cell. The samples are inserted into the cells using a syringe with a blunt nose needle. Up to five cells can be stacked together and once assembled and filled, the stack is rotated continuously on the axis perpendicular to the dialysis membranes on a spit-like mechanism. Four rows of cells can be placed on top of one another in the dialyzer such that a maximum of twenty cells can be utilized at one time. One problem with this spatial orientation is that it requires continuous rotation of the cells so that the samples remain in constant contact with the dialysis membrane so as to avoid concentration polarization. Another problem is that air bubbles which become trapped against the dialysis membrane slow down or prohibit dialysis. To solves these problems, U.S. Pat. No. 6,776,908 provides an equilibrium dialysis device comprising a body, comprising a surface having a first plane and a bottom surface having a second plane, the body is containing ninety-six wells arranged in an 8×12 array. Each of the wells is separated into a first side and a second side, by means for vertically separating the well, such that both sides of each well are fully open and accessible from the top surface of the body and closed on the bottom surface, wherein the body of the device comprises the material polytetrafluoroethylene, and wherein the means for vertically separating the well include dialysis membranes.

More particularly, this document details a multi-well dialysis plate designed to be reusable. The concept utilizes 8 strips of membrane that are sandwiched between Teflon® plates, which form the 96 well array, and sealed by clamp compression. There are several problems with this design. Notably there exists the potential for cross talk between the 12-wells associated with each strip. In other words, fluid can migrate from adjacent well to adjacent well by capillary action of the membrane. The design relies on compression of the Teflon® to seal off each well. Since Teflon® is relatively soft, it is conceivable that the wells furthest from the clamping rods will have the least amount of seal compression.

SUMMARY OF THE INVENTION

Thus, there is a particular need for improved device for conducting dialysis assays.

Broadly, the present invention discloses a dialysis apparatus, comprising:
a body with two planar sides,
wells contained in the body, the wells being accessible from one planar side,
a plurality of membranes for separating the wells into compartments, wherein each of said membranes is isolated one from another.

The dialysis apparatus may further comprise one or more of the following features and characteristics:
each of said membranes is in the form of a flat sheet;
the membranes extends transversally to the planar sides;
the apparatus further comprises plates, the body comprising an assembly of the plates;
the plates contain the compartments, a well being formed by a compartment of a plate facing a compartment of another plate;
the plates sandwich the membranes, a membrane separating the wells into two compartments;
the plates contain a recess surrounding the compartments, the membranes being received in the recesses;
the apparatus further comprises a carrier supporting a row of membranes, each membrane being isolated one from another by the carrier;
the carrier is comb-shaped with fingers delimiting cells for receiving the membranes;
the carrier is of pressure sensitive adhesive material;
the apparatus further comprises mechanical fastener for fastening the plates together;
the apparatus comprises an 8×12 array of wells.

The invention also relates to a method for assembling a dialysis apparatus, the dialysis apparatus comprising
a body with two planar sides,
plates forming the body, the plates containing compartments,
wells contained in the body, the wells being accessible from one planar side,
a plurality of membranes for separating the wells into compartments, wherein each of said membranes is isolated one from another, the method comprising the steps of:
providing said plates,
placing said membranes between the plates, such that each of said membranes is isolated one from another,
fastening the plates together.

The method may further comprise one or more of the following features and characteristics:
the apparatus further comprises at least one carrier supporting rows of membrane, the step of placing the membranes between the plates consisting in placing said at least one carrier between the plates;
the carrier is of pressure sensitive material, the step of fastening the plates consisting in exerting a pressure on the apparatus in order to cause the plates to stick together.

Further, the method described may be embodied in the dialysis apparatus described above.

BRIEF DESCRIPTION OF THE DRAWINGS

Other features, characteristics and advantages of the present invention will appear to the person of ordinary skill in the art in view of the detailed description below, made with reference to the annexed drawings, in which:

FIGS. 3 and 4 are perspective view of plates forming the apparatus of FIG. 1.

FIG. 5 is a perspective view of a detail of FIG. 4.

FIG. 6 is a perspective view of the membranes.

DETAILED DESCRIPTION OF THE DRAWINGS

According to the present invention, an apparatus is described for dialysis procedures. The apparatus comprises a body with wells contained in the body. The apparatus further contains dialysis membranes separating the wells into compartments, each of said membranes being isolated one from another. This makes it possible to avoid migration of the fluid contained in the wells from adjacent well to adjacent well, notably by capillary action of the membrane.

Figure 1:
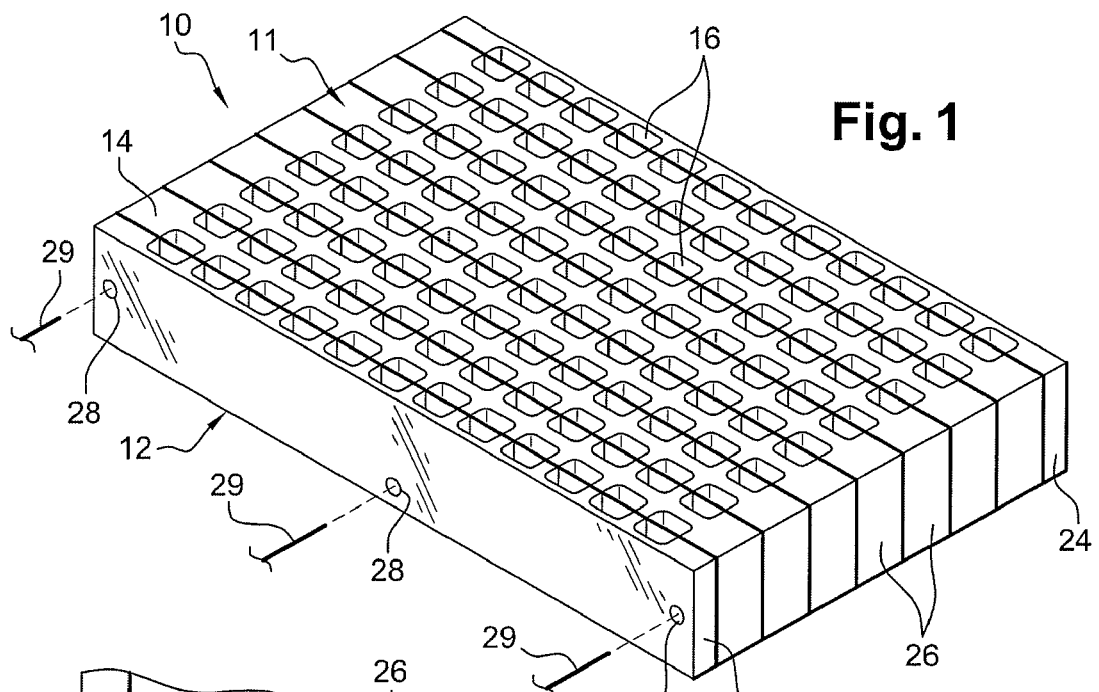
FIG. 1 is a perspective view of one embodiment of a dialysis apparatus incorporating features of the present invention.

FIG. 1 shows a perspective view of one embodiment of dialysis apparatus 10. The apparatus 10 contains a body 11 having a first planar side 12 and a second planar side 14. The apparatus 10 also comprises any number of wells 16. Sample to be tested or analyzed is introduced into the wells 16. The body is made from polytetrafluoroethylene (PTFE) or polypropylene, polysulfone, acrylic, polystyrene or PET, or any suitable material for molding life science labware products. For machined parts PTFE, polypropylene, polysulfone or acrylic is preferred. The size of the body is determined according to the number and the size of the wells 16. The thickness of the body is larger than the depth of the wells 16.

The body 11 may be constructed from a number of plates connected together as explained below. Each well 16 is like a cavity open on planar side 14 and accessible from one planar side, for example from side 14 which is considered hereinafter as the top side. This makes it possible to have access to the interior of the wells 16 at any time during usage. Especially the wells 16 are fully open at the top side 14, access to the wells 16 being thus easy.

Figure 3:
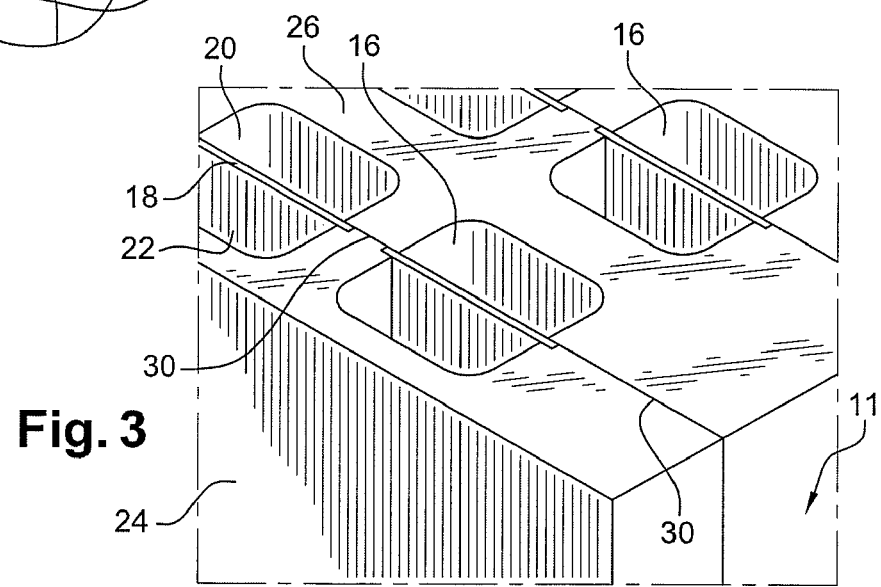

The body 11 is constructed by connecting plates 24, 26 of equivalent height and length to form a unified body or homogeneous unit. The plates 24, 26 are connected side-by-side together so as to form the wells 16. Preferably, there are two types of plates 24, 26. FIGS. 3 and 4 show perspective views of the plates 24, 26. FIG. 3 shows a perspective view of an end plate 24, the body 11 comprising two end plates 24. Between the end plates 24, the body comprises any number of mid plates 26 shown on FIG. 4. The assembly of these plates 24, 26 side-by-side makes it possible to insert membranes between the plates 24, 26 while the plates are assembled. This makes the assembly of the apparatus 10 easier. As an example, FIG. 1 shows two end plates 24 and seven mid plates 26. The plates can be machined or molded, although molding will significantly reduce overall product cost.

The apparatus 10 may further comprise alignment pins 29 in order to align the plates 24, 26. The alignment pins 29 may be of various shapes. The alignment pins 29 may be in the form of lateral rods, the edges of the plates 24, 26 being slid within the lateral rods; alternatively, the alignment pins 29 may be inserted within the plates 24, 26. FIGS. 3 and 4 show holes 28 performed in the plates 24, 26 adapted to receive the alignment pins 29. Any number of holes 28 may be provided. For example, the plates may be properly provided with one hole 28 at each of their extremities in order to facilitate the assembly of the plates 24, 26; additionally, and as depicted on FIGS. 3 and 4, the plates 24, 26 may be provided with a third hole 28 in the middle region between the two first holes 28.

The wells 16 are in the form of a deep cavity. The wells 16 are formed in the body 111 by any means, for example by drilling or molding. The sizes of the wells 16 are determined by the volume of sample to be tested. Roughly, the sizes of the wells 16 correspond to twice the volume of sample to be tested. The wells 16 are of any number; FIG. 1 depicting 96 wells arranged in an 8×12 array (8 rows, 12 columns). The wells 16 (number and sizes) are thus compatible with standard 96-well format laboratory supplies and equipment.

The well 16 may be formed by the assembly of the plates 24, 26. As exemplified in FIGS. 3 and 4, the plates 24 and 26 features compartments 20, 22. On FIGS. 3 and 4, the plates 24, 26 feature twelve compartments along one side. The compartments 20, 22 may be obtained while the plates are molded or formed by drilling into the plates 24, 26, although molding reduces significantly the cost of the construction. The compartments of a plate are open towards the top surface 14 and towards the adjacent plate. When the plates 24, 26 are assembled side-by-side, the compartments 20 of one plate correspond to the compartments 22 of the adjacent plate; the wells 16 may thus be formed by two adjacent compartments 20, 22. In the example of FIGS. 1 and 4, the mid plates 26 comprise compartments 20, 22 on opposite sides; the mid plates 26 being able to form wells 16 with two adjacent plates, one adjacent plate on each side of the mid plate 26. The compartments of a mid plate are open towards the top surface 14 and towards the adjacent plates on each side of said mid plate. As shown on FIGS. 1 and 3, the end plates 24 feature compartments only on one side; the other side is flat and corresponds to a side of the body 11. The compartments of an end plate are open towards the top surface 14 and towards the adjacent plate. Thus the end plates 24 form wells with only one adjacent plate. It is also possible for the mid plate 26 to feature compartments only on one side. FIG. 1 depicts two end plates 24 and seven mid plates 26, the plates forming ninety-six wells 16. Of course, it is possible to the plates to encompass more or fewer compartments in order to obtain more or fewer wells 16 in the body 11.

Figure 2:
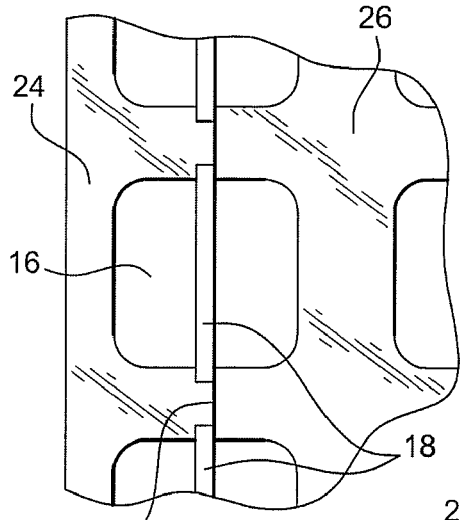
FIG. 2 is a detailed view of the embodiment shown in FIG. 1.

FIGS. 1, 2 and 6 show dialysis membranes 18. The membranes 18 are semi-permeable in that they allow solutes to pass through the membrane pores in a sieve-like fashion according to solute molecular weights, thus allowing some molecules to pass while preventing others from diffusing through the membrane pores. The membranes 18 are preferably in the form of flat sheets; the advantages are that the membranes 18 are of simple construction and the assembly of the membranes 18 to the body 11 is easy. The membranes 18 are disposed transversally to the planar sides 12, 14 as shown on FIG. 1. The height of the membranes 18 depends on the volume of the sample to be received in the wells 16. Preferably the membranes are at least as high as the wells 16 are deep; thus the entire depth of the wells 16 is separated by the membranes 18. The membranes 18 may extend from the planar side 14 to at least the bottom of the wells 16. The membranes 18 separate the wells 16 into compartments; this can be seen on FIG. 2 which is a detail perspective view of FIG. 1. Preferably, the membranes 18 separate the wells 16 into two compartments 20, 22, one of the compartments being a donating compartment 20, the other of the compartments being a receiving compartment 22. The donating compartment 20 contains the sample to be tested; the receiving compartment 22 contains a dialysis serum.

Advantageously, each of the membranes 18 is isolated one from another. In other words, the apparatus employs one discrete membrane per well, unlike the 12-well strip method of U.S. Pat. No. 6,776,908. This makes it possible to create the membrane seal and eliminate well-to-well cross talk. Once assembled, all leakage paths between wells are sealed. On FIG. 1, each well 16 of the 8×12 array is isolated from the surrounding wells. In other words, the wells 16 are isolated from the other wells of the same column and particularly from the other wells of the same row. Thus, the apparatus 10 avoids the migration of fluid from adjacent well to adjacent well by capillary action of the membrane.

According to one embodiment, the membranes 18 are formed as individual membranes, or in other words, as independent membranes. The membranes can be handled independently one from another. The membranes 18 are sandwiched between two adjacent plates 24, 26. Two adjacent membranes are fully separated, making it possible to create the membrane seal and eliminate well-to-well cross talk.

According to a preferred embodiment, a number of membranes 18 are held by a membrane carrier or frame 30. FIG. 6 depicts a perspective view of membranes 18 held by a carrier 30. The advantage of such an embodiment is that the assembly of the apparatus is simplified. Indeed, by holding "n" membranes, handling of the carrier 30 reduces membrane handling by a factor of "n"; on FIG. 6, the carrier 30 holds twelve membranes 18, thus reducing membrane handling by a factor of 12. Preferably, the carrier 30 supports all the membranes of a row. The carrier 30 isolates each membrane one from another. The carrier 30 may be comb-shaped, fingers 32 delimiting cells 34, each cell 34 receiving a membrane. Advantageously, but not necessarily, the cells 34 have the shape of the wells in cross-section transversally to the planar sides 12, 14. According to the example of FIG. 6, the cross-section of the wells transversally to the planar sides 12, 14 has a U-shape. The membranes 18 sit in the cells 34 of the carrier 30, and are isolated one from another thanks to the fingers 32. The edges of the membranes 18 are held by the carrier 30. More particularly, the membranes 18 are superposed on the carrier, the edges of the membranes 18 resting on the fingers 32 of the carrier. Thus, the membranes 18 are embossed relatively to on side of the carrier 30, the opposite side of the carrier 30 being flat. During assembly of the apparatus 10, the carrier 30 is sandwiched between two plates 24, 26. The carrier 30 locates each membrane 18 between two compartments 20, 22, the wells 16 being formed with two compartments 20, 22 separated by the membrane 18. Preferably, one carrier 30 is placed between two adjacent plates 24, 26. On FIG. 1, eight carriers 30 are used between the plates 24, 26 to position the membranes 18 between the compartments 20, 22. The carriers 30 are preferably of the same length and of the same height as the body 11. FIG. 2 depicts the carrier 30 and the fingers 32 running along the top side 14 of the body 11.

The material of the carrier 30 is preferably chosen among materials permitting isolation of the membranes 18 one from another. Especially, the material of the carrier 30 is non-porous, thus avoiding all leak paths between membranes 18. On FIG. 2, on the top side 14, each of the membranes 18 can be seen to be isolated one from another of the same rows by a finger 32 of the carrier 30; the same separation occurs along the depth of the wells towards the planar side 12. Also, the carrier 30 may be of an adhesive material. This makes it possible to bind the plates 24, 26 together. For example, the carrier 30 is of a pressure sensitive adhesive (PSA) material. When the plates 24, 26 are assembled and pressed together, the carrier 30 ensures the assembly of the apparatus 10. Thus it is even possible to avoid the use of any further mechanical fasteners to assemble the plates; the advantage is the reduction of the cost of the apparatus 10. Nevertheless, it is still possible to use further mechanical fastener to improve the assembly of the plates 24, 26. The types of mechanical fasteners available for use would include screws, pins or mold-in place liquid fastener. The preferred embodiment of the apparatus would not require a secondary mechanical fastener, however, in the event that a secondary fastener is required, it is preferably of the mold-in type applied into the alignment pins.

The carrier 30 may be provided with holes 28, alignment pins 29 of the plates 24, 26 ensuring the alignment of the carrier 30 with respect to the plates 24, 26, and therefore, the alignment of the membranes 18 with respect to the compartments 20, 22 of the wells 16.

The plates 24, 26 may be provided with recesses 36 in order to accommodate the membranes 30. FIG. 5, showing a perspective view of a detailed compartment 20, 22 of a mid plate 26, depicts an example of the recess 36. The recesses 36 make it possible to position the membranes 18 between two plates 24, 26. The membranes 18 have a certain thickness. Preferably, the membranes have a thickness ranging from 0.0001 to 0.100 inch and most preferably from 0.0005 to 0.020 inch. The recesses 36 make it possible to ensure that the membranes 18 are imbedded in the membrane receiving side of the plates, said side becoming flat; this allows assembly flat sides of plates 24, 26 and improvement of the tightness of the wells 16. The membranes 18 are sandwiched by two sides of respective plates 24, 26; one of the sides features the recesses 36 to accommodate the membranes 18, the other side being flat. Thus, once the membranes 18 are accommodated in the respective recess 36, the two sides are flat and may be properly assembled. A plurality of embodiments to provide the plates 24, 26 with recesses 36 are possible. According to one embodiment, every second mid plate 26 is provided with recesses 36 on both sides, the others mid plates 26 being recess free. According to the number of mid plates 26 used, both, one or none of the end plates are provided with recesses 36. Preferably, each mid plate 26 has recesses 36 only on one side, the opposite side of said mid plate 26 being recess free; only one of the two end plates may thus have the recesses 36 on the side having the compartments 20, 22.

If a carrier 30 is used, it was mentioned that the membranes are embossed relative to one side of the carrier 30, the opposite side of the carrier 30 being flat. The carrier 30 is thus positioned with respect to the plates 24, 26 in order to accommodate the membranes 18 in the recesses 36 of one of the two plates. The flat side of the carrier 30 is faced to the flat side of the other plate.

Contrarily to the re-usable device of U.S. Pat. No. 6,776,908, the apparatus 10 of the present invention is preferably disposable. Indeed, in order to avoid cross contamination of the membranes between uses, a re-usable device requires validation for cleaning and storage between uses; also, it is not practical to expect the end user to assemble for example ninety-six membranes pieces in an assembly. The apparatus of the present invention eliminates the end user as a factor in evaluation of test results because the apparatus is supplied ready for use and is designed to be disposable. Lastly, the apparatus will also conform to the physical form prescribed by the current SBS Standard for MicroPlates (ANSI/SBS-2004).

During assembly of the apparatus, a first end plate 24 is disposed on one or several alignment pins 29 (in the example, three pins are used), the pins 29 being for example inserted in the holes 28. Before a mid plate 26 is placed on the alignment pins 29, membranes 28 are placed along the side of the end plate 24 having compartments 20, 22; if the carrier 30 is used, the pins 29 are introduced in the holes 28 of the carrier 30 until the carrier rests along the side of the end plate 24 having compartments 20, 22. The process continues by placing further mid plates 26 on the alignment pins 29, membranes 18 or carriers 30 supporting membranes being interposed between two plates. Eventually, the second end plate 24 is placed on the alignment pins 29 along the last set of membranes or along the last carrier 30. During the process, care is taken to accommodate the membranes 30 within the recesses 36 of the plates. Once the plates 24, 26 and membranes 18 are assembled, mechanical fasteners can be placed in order to prevent leakage. For example, bolts are screwed on the pins 29. Preferably, three mechanical fasteners are used, two along the sides of the body 11 and one along the middle of the body 11; this ensures the prevention of leakage in the wells furthest from the mechanical fasteners. If carriers 30 of PSA are implemented, pressure is exerted on the plates in order to stick the plates together; more particularly, the two end plates 24, 26 are pressed one towards the other. In such case, mechanical fasteners can be omitted. Alternatively, glue can be injected in the alignment pin holes. The glue solidifies and increases the tensile strength to resist separation if the unit is pulled. Another alternative is to have the alignment pin with a threaded ends such that is can be permanently fastened and left in place. Unlike the device according to U.S. Pat. No. 6,776,908 where one membrane is placed in each of the eight separation planes, the present apparatus comprises a single membrane per well, i.e., each of the membranes is isolated one from another.

What is claimed is:

1. A dialysis apparatus comprising:
   a body with two planar sides, the body comprising an assembly of plates,
   wells contained in the body, the wells being accessible from one planar side,
   a plurality of membranes for separating the wells into compartments, wherein each of said membranes is isolated one from another, and
   a carrier supporting a row of the membranes, each membrane being isolated one from another by the carrier;
   wherein the carrier is of pressure sensitive adhesive material.

2. A dialysis apparatus, comprising:
   a body with two planar sides,
   wells contained in the body, the wells being open and accessible from one planar side, and closed on the other planar side,
   a plurality of membranes for separating the wells into compartments, each of said membranes being isolated one from another,
   at least one carrier, each of said carriers supporting a row of membranes.

3. The apparatus of claim 2, wherein the carrier is of pressure sensitive material.

4. The apparatus of claim 2, further comprising plates forming the body, the plates sandwiching the carriers.

5. The apparatus of claim 4, the plates containing the compartments, a well being formed by a compartment of a plate facing a compartment of another plate.

6. The apparatus of claim 5, wherein a recess surrounds each compartment, the membranes being received in the recesses.

7. The apparatus of claim 2, wherein each of said membranes is in the form of a flat sheet.

8. The apparatus of claim 7, wherein the membranes extend transversally to the planar sides.

9. The apparatus of claim 2, further comprising plates, the body comprising an assembly of the plates, the plates sandwiching the membranes.

10. The apparatus of claim 9, the plates containing recesses surrounding the compartments, the membranes being received in the recesses.

11. The apparatus of claim 9, further comprising mechanical fastener for fastening the plates together.

12. The apparatus of claim 2, each membrane being isolated one from another by the carrier.

13. The apparatus of claim 2, wherein the carrier is comb-shaped with fingers delimiting cells for receiving the membranes.

14. The apparatus of claim 2, comprising an 8×12 array of wells.

15. A method for assembling a dialysis apparatus, the dialysis apparatus comprising
   a body with two planar sides,
   plates forming the body, the plates containing compartments,
   wells contained in the body, the wells being accessible from one planar side,
   a plurality of membranes for separating the wells into compartments, wherein each of said membranes is isolated one from another,
   at least one carrier supporting a row of membranes,
   the method comprising the steps of:
   providing said plates,
   placing said carrier supporting a row of membranes between the plates, such that each of said membranes is isolated one from another,
   fastening the plates together.

16. The method of claim 15, wherein the at least one carrier is of pressure sensitive material, the step of fastening the plates consisting in exerting a pressure on the apparatus in order to cause the plates to stick together.

* * * * *